Figure 3:
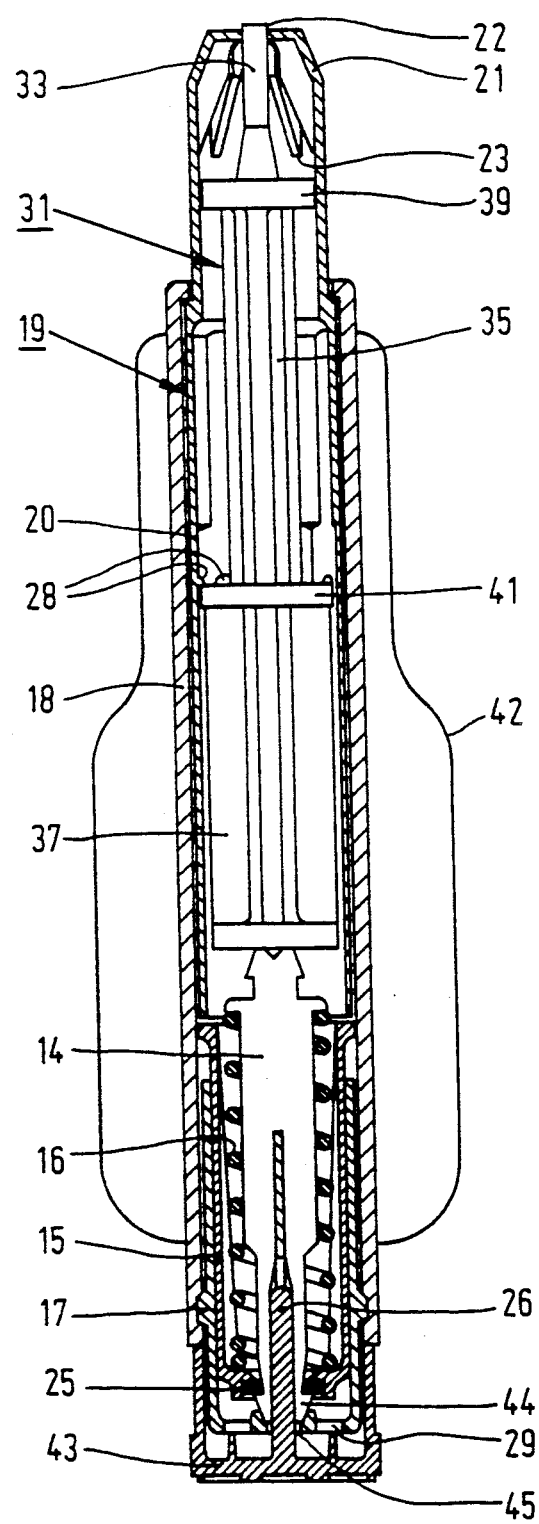
Figure 3:
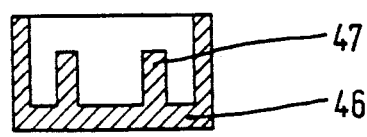

United States Patent [19]

van der Wal

[11] Patent Number: 5,071,353

[45] Date of Patent: Dec. 10, 1991

[54] TRAINING DEVICE FOR AN AUTOMATIC INJECTOR

[75] Inventor: Gillis P. van der Wal, Olst, Netherlands

[73] Assignee: Duphar International Research B.V., Weesp, Netherlands

[21] Appl. No.: 597,351

[22] Filed: Oct. 10, 1990

[30] Foreign Application Priority Data

Oct. 16, 1989 [NL] Netherlands .......................... 8902553

[51] Int. Cl.$^5$ ...................... G09B 23/28; A61M 5/20
[52] U.S. Cl. .................................. 434/262; 604/134; 604/135
[58] Field of Search ................ 604/134, 135, 136, 68; 173/121; 434/262; 72/433, 434; 401/81, 180, 54

[56] References Cited

U.S. PATENT DOCUMENTS

| | | | |
|---|---|---|---|
| 3,563,098 | 2/1971 | Gley | 604/135 |
| 3,625,208 | 12/1971 | Frost et al. | 604/68 |
| 3,712,301 | 1/1973 | Sarnoff | 604/136 |
| 3,795,061 | 3/1974 | Sarnoff et al. | 434/262 |
| 4,167,350 | 9/1979 | Harris | 401/81 |

FOREIGN PATENT DOCUMENTS 741104 5/1943 Fed. Rep. of Germany ...... 401/180

*Primary Examiner*—Richard J. Apley
*Assistant Examiner*—Karen G. Horowitz

*Attorney, Agent, or Firm*—Stevens, Davis Miller & Mosher

[57] ABSTRACT

The invention relates to a training device for an automatic injector. The device comprises a cylindrical outer sleeve in the rear portion of which a discharge mechanism is connected and in the front portion of which a holder intended for accommodating a punch member is incorporated so as to be locked against forward movement. The discharge mechanism comprises a plunger, a coil spring which acts on the plunger, a locking device and a safety member. The holder for the punch member comprises a sleeve-like rear portion which is open at each end. The punch member is accommodated in the holder such that its rear end at least substantially engages the front end of the plunger, and such that the front prod-shaped end portion which has dimensions such that it can pass through the central aperture in the nose portion of the holder outwards, is present within the holder prior to use of the device. The device further comprises auxiliary means for making the device ready for reuse. The rear end portion of the punch member comprises means which, in cooperation with means provided on the inner wall of the sleeve-like rear portion of the holder, prevent undesired forward movement of the punch member in the holder, in which, however, the device at the area of the means is proportioned such that, after activation, the wall of the holder can expand resiliently outwards within the outer sleeve to allow the punch member to pass.

2 Claims, 2 Drawing Sheets

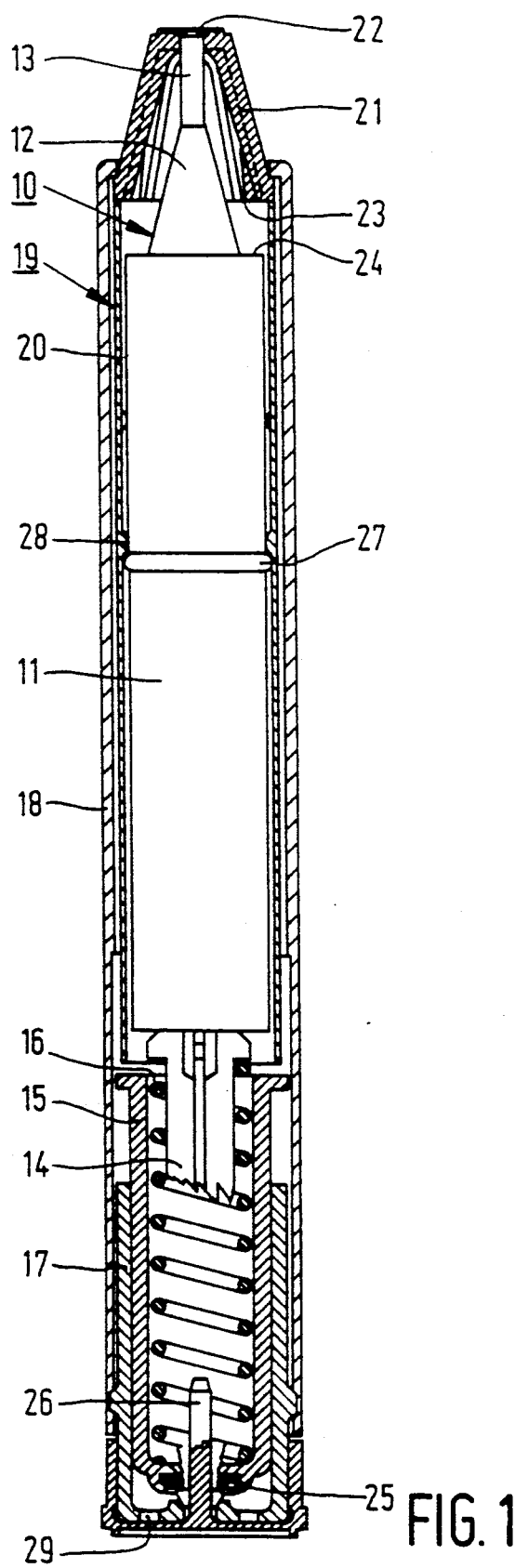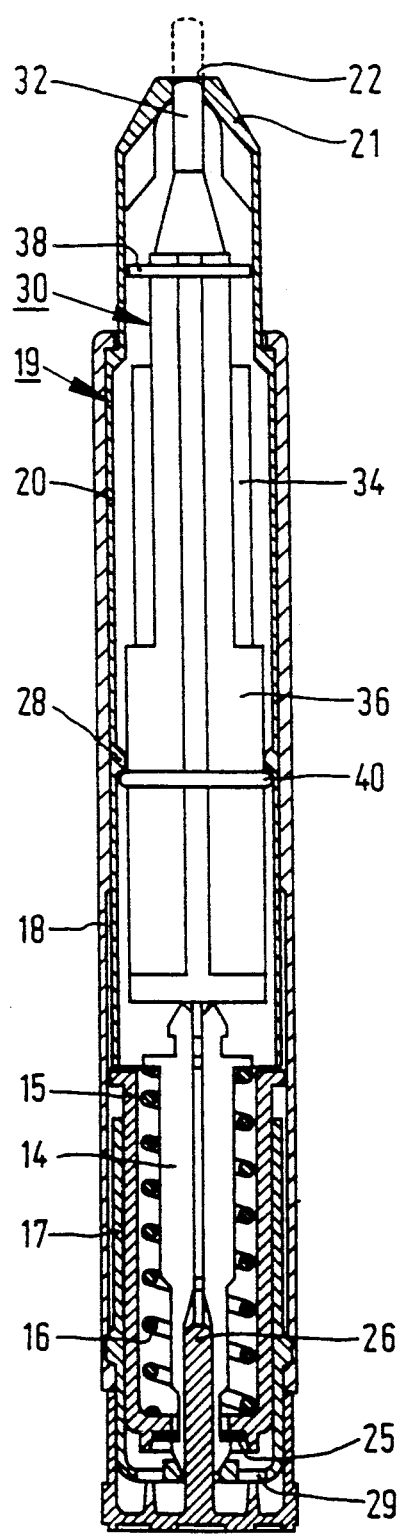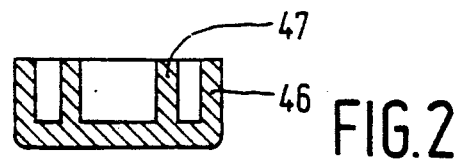
FIG. 1  FIG. 2

TRAINING DEVICE FOR AN AUTOMATIC INJECTOR

The invention relates to a training device for an automatic injector, comprising a cylindrical outer sleeve in the rear portion of which a discharge mechanism is connected and in the front portion of which a holder intended for accommodating a punch member is incorporated so as to be locked against forward movement.

The discharge mechanism comprises an inner pistol sleeve which is open at its front end, a plunger which is movable in said pistol sleeve, a coil spring which acts on said plunger and tries to move same out of the front end of the inner pistol sleeve outwards, a locking device which cooperates with said plunger so as to prevent undesired forward movement thereof, and a safety member to block unintentional unlocking of the locking device.

The holder for the punch member comprises a sleeve-like rear portion which is open at each end and which, after activating the device, is traversed by a rear end portion of the punch member, and a nose portion which comprises a central aperture and which serves to stop the forward movement of the punch member in the holder after activating the device and to allow the front end portion of said member to pass.

The punch member is accommodated in the holder so that its rear end at least substantially engages the front end of the plunger and the front prod-shaped end portion, which has such dimensions that it can pass through the central aperture in the nose portion of the holder outwards, is present within the holder prior to use of the device.

An auxiliary means is present for making the device ready for reuse.

Such a device is known from U.S. Pat. No. 3,795,061, with the proviso that the inner pistol sleeve for the discharge mechanism forms one assembly with the holder and that the nose portion of the holder constitutes a separate component ("end cap").

Automatic injectors are designed in particular for use by persons who, at a given instant which is not known beforehand, have to administer an injection into their own body. Such persons include, for example, soldiers after having been exposed to an enemy's battle gas, for example, a nerve gas. It will therefore be obvious that the user may not hesitate to inject himself at the critical moment when the injection is required. As a matter of fact, the user's life will at that instant depend on the accurate manipulation of the injector. The rapid and accurate use of an automatic injector is also a first requirement in the so-called "buddy help", giving help to a wounded and/or panicked buddy in the battle field. An automatic injector intended especially for this purpose has also been developed. The fear of administering to oneself or a buddy an injection at a critical moment must hence be overcome previously by training.

The following requirements have to be imposed upon such a training device:

(1) the training device must simulate the action of the automatic injector as well as possible, of course without the injection being administered, and (2) it must be possible to use the training device over and over again and to make the training device ready for reuse very easily.

It is exactly with respect to the second requirement that the training device described in U.S. Pat. No. 3,795,061 is unsatisfactory. This known training device comprises a return spring which, after activating the device, serves to partially compensate for the driving force of the driving spring before the forward movement of the punch member is stopped by the end cap. However, in order to satisfy the first requirement, the force with which the front prod-shaped end portion of the punch-member emanates outwards from the nose of the device must be very considerable. As a matter of fact, the device in use must simulate as readily as possible the automatic injector which must comprise a powerful driving spring to overcome the resistance when injecting through the battle dress. In order to also overcome the resistance of the return spring, a very powerful driving spring must hence be used. As a result of this, the training device will be subject to greater detrition during use, so that the reuse is restricted. It has been found that a training device as described in U.S. Pat. No. 3,795,061 can at best be used only ten times, whereas the military authorities impose the requirement that such a device must be usable at least approximately fifty times. In preparing the device for reuse, the spring force of the driving spring must be overcome; the oppositely directed spring force of the return spring contributes to this "recocking" of the driving spring. However, during said recocking, not only does the spring force of the driving spring increase, but the compensating force exerted by the return spring decreases. As a result of this, the recocking of the driving spring, in particular the last phase hereof, is impeded. So the construction with two coil springs as is known from the above United States Patent is an impediment in making the device ready for reuse.

In order to meet the above-mentioned disadvantages, in U.S. Pat. No. 4,640,686 it is proposed to use a training device for an automatic injector which produces an audible signal. However, the disadvantage of such a device is that in use the action of an automatic injector is insufficiently simulated. The forces occurring during the use of an automatic injector give the user a certain emotional sensation which is quite different from an audible signal.

It is the object of the present invention to provide a training device for an automatic injector which can be used considerably more frequently that the device known from U.S. Pat. No. 3,795,061 and which can be made ready for reuse much more easily.

This object can be achieved by means of a training device as described in the opening paragraph which is characterised according to the present invention in that the rear end portion of the punch member comprises means which, in cooperation with means provided on the inner wall of the resilient sleeve-like rear portion of the holder, prevent undesired forward movement of the punch member in the holder, in which, however, the device at the area of said means is proportioned so that after activation the wall of the holder can expand resiliently outwards within the outer sleeve so as to allow the punch member to pass.

It has been found that the use of the above-mentioned means on the punch member and on the inner wall of the holder makes the use of a return spring superfluous. As a result of this, a less powerful driving spring will suffice to nevertheless obtain optimum simulation, i.e. to give the user a sensation which resembles as well as possible the sensation he gets from an injection with an automatic injector. Omitting the return spring facilitates the recocking of the driving spring and hence the preparing of the device for reuse. Furthermore it has been found surprisingly that the number of times the training device may be reused has been increased considerably by omitting the return spring and using the above-described measures. It has been found that the training device according to the invention can readily be used fifty times. An extra advantage of the device according to invention over the known device is the reduction in cost-price by omitting one component, namely the return spring; in addition, this simplifies the assembly.

In a favorable embodiment the device according to the invention is constructed so that the rear end portion of the punch member comprises a circumferential externally projecting ridge or an annular member the front face of which engages a plurality of radially arranged, inwardly projecting raised portions which are provided on the inner wall of the sleeve-like rear portion of the holder, said portion having a five-to fourteen-sided cross-section, the ridge or the annular member on the punch member and the raised portions on the inner wall of the holder being mutually proportioned so that after activating the device the raised portions are pushed aside ("overridden") by the ridges or by the annular member so that the forward movement of the punch member in the holder is then not impeded. A holder is preferably used which comprises raised portions on the inner wall, as described in European Patent Specification 0,186,916. The holder known from this Patent Specification is intended for an automatic injector and has for its object to improve the shock resistance of the injector, namely to prevent that, when the injector is dropped, the cartridge in the holder moves forward so that the tip of the needle can emanate.

As stated hereinbefore, the nose portion of the holder serves to stop the forward movement of the punch member in the holder after activating the device. For that purpose, for example, the nose portion may be reinforced by means of a plurality of longitudinal ribs which at their rear ends constitute an abutment for the punch member. It is of advantageous to have the possibility of adjusting the "stroke" of the punch member as desired, i.e. the distance over which the prod-shaped end portion of the punch member can emanate from the central aperture in the nose portion of the holder. According to another aspect of the invention this has proved to be possible by connecting an annular member around the punch member at a given distance from the front end of said punch member. The "stroke" is now determined by the distance between the front face of said annular member and the abutment in the nose portion of the holder.

In U.S. Pat. No. 3,795,061 mentioned hereinbefore a certain auxiliary means is used to enable the device to be ready for reuse: "a recocking tool". Such an auxiliary means may be used when the nose portion and the sleeve-like rear portion constitute separate components of the holder, in a construction in which the discharge mechanism in the cylindrical outer sleeve is connected to an outer pistol sleeve within which the inner pistol sleeve can be moved, as is shown for an automatic injector, for example, in European Patent Specification 0,186,916. The auxiliary means for making the device ready for reuse may advantageously be a cap which fits around the outer pistol sleeve and which comprises at least two rod-shaped members extending within the cap. The rod-shaped members correspond to apertures recessed in the rear wall of the outer pistol sleeve and, upon using the cap, can move the inner pistol sleeve forward with respect to the outer pistol sleeve and can fix it in this position, as a result of which the discharge mechanism can be locked. In fact, by fixing the inner pistol sleeve with the auxiliary means while the punch member and hence the plunger are pushed backwards in the cylindrical outer sleeve, the plunger is again locked against undesired forward movement.

The invention will now be described in greater detail with reference to the preferred embodiments which are presented in the drawings, in which FIGS. 1, 2 and 3 show training devices according to the invention, partly as a cross-sectional view, partly broken away and as a side elevation.

The training device shown in FIG. 1 comprises a punch member 10, the rear end portion 11 of which has a substantially uniform diameter throughout its length and the prod-shaped front end portion 13 of which is connected to the rear end portion via a conical intermediate portion 12. The rear end of the punch member engages or substantially engages the front end of a plunger 14 which, together with an inner pistol sleeve 15, keeps a coil spring 16 as a power source enclosed. The inner pistol sleeve can be moved axially within an outer pistol sleeve 17 which is locked in an outer sleeve 18, which also keeps a holder 19 for the punch member locked to prevent forward movement. The holder comprises a sleeve-like rear portion 20 having a twelve-sided cross-section and a nose portion 21 having longitudinal ribs and a central aperture 22. This aperture is proportioned so that after activating the device, the prod-shaped front end portion 13 of the punch member can emanate through the aperture. The rear end 23 of the longitudinal ribs in the nose portion constitutes an abutment for the shoulder 24 formed by the conical intermediate portion 12 of the punch member. The "stroke" is determined by the distance between the shoulder and the abutment thereof in the nose portion of the holder. The device further comprises a locking device 25 for the plunger 14 and a safety member in the form of a cap having a pin 26 extending axially therein. Locking and safety will be described in greater detail with reference to FIG. 3. The punch member comprises a circumferential outwardly projecting ridge 27 whose front face engages a number of raised portions 28 radially situated on the inner wall of the resilient sleeve-like portion 20 of the holder. The circumferential ridge on the punch member, in cooperation with the raised portions 28, prevents undesired forward movement of the punch member in the holder. After activating the device, the punch member is moved forward by the releasing spring 16, the ridge easily passing the raised portions on the inner wall of the holder. The resilient wall of the sleeve-like portion of the holder expands at the area of the raised portions. The forward movement of the punch member in the holder is stopped when the shoulder 24 contacts the abutment formed by the longitudinal ribs in the nose 21 of the holder. The prod-shaped front end portion 13 of the punch member has then emanated over a length equal to the "stroke". After use, the device may again be made ready for reuse by means of a suitable auxiliary means. This auxiliary means must ensure that, when the prod-shaped end portion is pushed inwards and the punch member and plunger are pushed backwards, the inner pistol sleeve remains in its place. It is then possible, as will be explained in greater detail hereinafter with reference to FIG. 3, to lock the device and hence to make it ready for reuse. A suitable auxiliary means herefor, to be described hereinafter with reference to of FIGS. 2 and 3, is a cap which comprises a number of rod-shaped members which upon use of the cap can extend through the associated apertures 29 in the outer pistol sleeve and in this manner can retain the inner pistol sleeve during recocking the spring.

The embodiments shown in FIGS. 2 and 3 comprise differently shaped punch members: 30 and 31, respectively. The front prod-shaped end portions 32 and 33 are connected, via portions 34 and 35 having a slightly larger diameter, to the rear end portions 36 and 37, which are movable in the sleeve-like portions 20 of the holders 19; these sleeve-like portions have a 7-sided cross-section. Annular members 38 and 39 are connected around the portions 34 and 35 at such a distance from the abutment formed by the longitudinal ribs in the nose portion 21 of the holder 20 that the prod-shaped end portions 32 and 33, after activating the devices, emanate over the desired distance. This distance is determined by the "stroke", i.e. the distance between the front of the annular member and the abutment in the nose of the holder. Annular members 40 and 41, which have the same functions as the ridge 27 in the FIG. 1 and engage with their front faces a plurality of raised portions radially situated on the inner wall of the resilient sleeve-like portion 20 of the holder, are connected around the rear end portions 36 and 37 of the punch members shown. Outer sleeve, discharge mechanism etc. of FIGS. 2 and 3 do not differ from those of FIG. 1; like components are referred to by like reference numerals. The device shown in FIG. 3 comprises two longitudinal wing-shaped projections 42 at its outside.

Locking, safety and recocking, i.e. making the device ready for reuse, will now be described in greater detail with reference to the device shown in FIG. 3. When the device is used, first the safety cap 43 with safety pin 26 is removed. The device is now equipped with its nose on a suitable place of the body, for example, the upper leg, and is pressed on. The holder 19 in the outer sleeve 18 is moved backwards, which results in a relative backward movement of punch member 31, plunger 14, and inner pistol sleeve 15 with respect to the outer pistol sleeve 17 which is locked in the outer sleeve. At its rear end, the plunger comprises four resilient prongs 44 which through an aperture in the rear wall of the inner pistol sleeve bear on a locking ring 25 which is situated around said aperture. Because the safety pin 26 has been removed, the resilient prongs, during the backward movement of the plunger, can move towards each other as a result of the conical tapering of a central aperture 45 in the rear wall of the fixed outer pistol sleeve. As a result of this, the prongs and hence the plunger are unlocked, as a result of which plunger and punch member shoot forward under the influence of the coil spring. In the extreme outward position of the prod-shaped front portion 33 of the punch member, the annular member 39 is stopped by the abutment 23 in the nose portion of the holder.

Upon recocking, an auxiliary means is used instead of the safety cap, which is also constructed in the form of a cap 46 which has two rod-shaped members 47. By arranging the cap on the rear end of the outer pistol sleeve in the correct manner, the rod-shaped members will extend through two apertures 29 in the rear wall of said pistol sleeve and can in this manner be pushed against the inner pistol sleeve. Upon recocking, the prod-shaped end portion of the punch member is pushed inwardly, the plunger also moving backwards. By moving during this process the inner pistol sleeve 15 forward with respect to the outer pistol sleeve by means of the cap 46 and by fixing it in this position, the resilient prongs of the plunger can be pushed through the central aperture in the rear wall of the inner pistol sleeve until they are locked on the locking ring 25. The device is now ready again for use.

I claim:

1. A training device for an automatic injector, comprising a cylindrical outer sleeve, a punch member having a front prod-shaped end portion, a discharge mechanism and auxiliary means for making the device ready for reuse;

wherein the discharge mechanism is connected to and disposed in the rear portion of the sleeve, and the front portion of the sleeve comprises a holder for accommodating the punch member such that the punch member is locked against forward movement;

the discharge mechanism comprises an inner pistol sleeve which is open at its front end, a plunger which is movable in the pistol sleeve, a coil spring which acts on the plunger and tries to move the plunger out of the front end of the inner pistol sleeve outwards, a locking device which cooperates with the plunger to prevent undesired forward movement thereof, and a safety member to block unintentional unlocking of the locking device;

the holder for the punch member comprises a sleeve-like rear portion which is open at each end and which, after activating the device, is traversed by a rear end portion of the punch member, and a nose portion which comprises a central aperture and which serves to stop the forward movement of the punch member in the holder after activating the device and to allow the front end portion of the punch member to pass;

the punch member is accommodated in the holder such that its rear end at least substantially engages the front end of the plunger, and its front prod-shaped end portion, which has dimensions such that it can pass through the central aperture in the nose potion of the holder outwards, is present within the holder prior to use of the device;

the rear end portion of the punch member comprises a circumferential outwardly projecting ridge or an annular member, the front of the ridge or the annular member engaging a plurality of radially arranged, inwardly projecting raised portions which are provided on the inner wall of the sleeve-like rear portion of the holder, the sleeve-like rear portion having a five- to fourteen-sided cross-section, the ridge or annular member of the punch member and the raised portions of the inner wall of the holder being mutually proportioned such that, after activating the device, the raised portions are pushed aside by the ridges or annular member so that the forward movement of the punch member in the holder is not impeded; and the rear end portion of the punch member comprises means which, in cooperation with means provided on the inner wall of the sleeve-like rear portion of the holder, prevent undesired forward movement of the punch member in the holder, in which the device at the area of the means is proportioned so that, after activation, the wall of the holder can expand resiliently outwards within the outer sleeve to allow the punch member to pass;

wherein the discharge mechanism is connected in the cylindrical outer sleeve by means of an outer pistol sleeve within which the inner pistol sleeve can be moved and the auxiliary means making the device ready for reuse comprises a cap which fits around the outer pistol sleeve and which comprises at least two rod-shaped members which extend within the cap and correspond to apertures recessed in the rear wall of the outer pistol sleeve and which, upon using the cap, can move the inner pistol sleeve forward with respect to the outer pistol sleeve and can fix it in this position, as a result of which the discharge mechanism can be locked.

2. A device as claimed in claim 1, characterised in that the nose portion of the holder constitutes an abutment for an annular member which is connected around the punch member at such a distance from said punch member that after activating the device the prod-shaped end portion emanates from the central aperture in the nose portion of the holder over the desired distance.

* * * * *